US00PP15784P2

(12) United States Plant Patent
Cosner et al.

(10) Patent No.: US PP15,784 P2
(45) Date of Patent: Jun. 7, 2005

(54) ***IMPATIENS* PLANT NAMED 'TILAV IMPROVED'**

(50) Latin Name: *Impatiens walleriana*
Varietal Denomination: TiLav Improved

(76) Inventors: Harlan B. Cosner, 14389 E. Evans Creek Rd., Rogue River, OR (US) 97537; Susan Cosner, 14389 E. Evans Creek Rd., Rogue River, OR (US) 97537

( * ) Notice: Subject to any disclaimer, the term of this patent is extended or adjusted under 35 U.S.C. 154(b) by 33 days.

(21) Appl. No.: 10/783,330

(22) Filed: Feb. 20, 2004

(51) Int. Cl.[7] ..... A01H 5/00
(52) U.S. Cl. ..... Plt./317
(58) Field of Search ..... Plt./317

*Primary Examiner*—Kent Bell
(74) *Attorney, Agent, or Firm*—Ganz Law, PC; Bradley M. Ganz

(57) ABSTRACT

A new double *impatiens walleriana* plant named 'TiLav Improved'; producing lavender flowers; dark green foliage; medium-vigorous growth habit; fully double flowers held above or beyond the foliage on strong peduncles and pedicels; and a compact mounded growth habit.

1 Drawing Sheet

Latin name of the genus and species and variety denomination: *Impatiens walleriana* plant and known by the cultivar name 'TiLav Improved'.

BACKGROUND OF THE INVENTION

Field of Invention

The present invention comprises a new and distinct cultivar of plant, botanically known as *impatiens walleriana* and hereinafter referred to by the cultivar name of 'TiLav Improved'.

1. The plants are useful in landscaping, window and hanging baskets and flower gardens.
2. The plant is an *Impatiens walleriana.*
3. The plants are generally classed as an annual bedding plant.

Description of the Relevant Prior Art

1. The pollen parent is an unpatented pollen producing double *impatiens walleriana* coded P-BR-131, and the seed parent is an unpatented semi-double *impatiens* coded M-BR-203. 'TiLav Improved' is both male and female sterile. Cultivar is both female and male sterile. Both parents are capable of both seed and pollen production.
2. The seed parent was a Pink flowered cultivar and the pollen parent was a Lavender flowered cultivar, neither parent is either patented or commercially available. The cross was made in the breeder's controlled breeding program at Rogue River, Oreg. by lateral stems with two or more leaves. The first asexual reproduction was also made at Rogue River, Oreg. Successive asexual generations produced from cuttings with two or more leaves have shown the cultivar to be stable and reproduced true to type.

COMPARISON

1. The plant is compared to 'TiLav', U.S. Plant Pat. No. 13,003.

2. The flower color of 'TiLav Improved' is lighter than that of 'TiLav'.
3. The Foliage color of 'TiLav Improved' is lighter than that of 'TiLav'.
4. 'TiLav Improved' flowers better in temperatures above 90° F. than 'TiLav'.
5. See comparison chart labeled Chart 1.

SUMMARY OF THE INVENTION

The cultivar is unique either in one or a combination of the characteristics described herein. It is a new, double *impatiens walleriana* producing lavender flowers; dark green foliage; medium-vigorous growth habit; fully double flowers held above or beyond the foliage on strong peduncles and pedicels; a compact mounded growth habit.

DESCRIPTION OF THE PHOTOGRAPHS

The attached color photographs illustrate a plant of 'TiLav Improved' grown in winter and just beginning to mature. The plant shown in the photographs is not the plant described in the specification; however, it is of the same cultivar. Variations between the written description and the colors in the photographs may occur due to the type of film and/or light reflectance and the type of light captured by the film. In the event there are such variations, the written description shall control.

PLANT DESCRIPTION

The following description was taken at Rogue River, Oreg. on Feb. 7, 2004. The description is of a plant of 'TiLav Improved' similar to the one shown in the photograph.

The following description was taken from a plant approximately 12-weeks of age under the following environment and cultural practices at Rogue River, Oreg. Phenotypical variations may result in plants grown under conditions and locations other than those listed herein.

Container: 6 inch azalea pot.
Medium: Peat-lite type of soilless medium.

Greenhouse covering: Double layer Polyethelene with 50% shade applied above the covering.
Minimum temperature: 65° F.
Maximum temperature: 75° F.
Light levels: 1000 to 1500 ft candles.
Fertilizer: 20-10-20 with trace elements applied twice followed by one leaching with clear water.
Cutting type: Lateral stems with two or more leaves.
Propagation:

*Type of cutting.*—Lateral stems with two or more leaves.

*Time to initiate roots.*—Generally about 7 to 10 days at soil temperature of 72° F.

Appearance and form of mature plant:

*Note.*—All size measurements for plant, stems, foliage, flowers, peduncles, pedicels, buds, and sepals are taken during winter, low light conditions when the above are the smallest. Spring and summer high light sizes are generally much larger than the sizes that are described below.

*Growth habit.*—Mounded and of compact-medium vigor.

*Plant size.*—Plants mature at about 20 cm in height and about 35 cm in width. Both of these measurements are a function of age, environmental and cultural practices, and can vary accordingly.

*Rooting habit.*—The roots are fibrous and well branched.

*Rooting ability.*—Easy, no hormones needed.

*Stems.*—Stems are freely produced, and no pinching to induce branching is needed. Color is translucent 146C to 146D with stippling on juvenile stems of very small markings that are difficult to determine but which appear to be close to 178A. The stippling is heaviest at the nodes. The stippling appears to be outgrown as mature stem color becomes solid 146C to 146D. The stems at maturity are generally at least 3 mm in diameter at the internodes, and the internode length is generally at least 0.5 cm in length.

*Foliage.*—Shape is ovate with cuneate to attenate base; crenate margin, margin having tiny spines of an undeterminable greenish color, and each being less than 1 mm in length and protruding outwards in a perpendicular direction from leaf edge and parallel to the flat surfaces of the leaf, between the lobes of the crenate margin; and an acuminate apex. Size of largest is about 3 cm long; about 2.75 cm wide.

*Foliage color.*—Adaxial surface close to 146A; abaxial surface close to 148D; adaxial surface venation is close to 146D at base, becoming barely distinguishable to undistinguishable towards the leaf margins; abaxial surface venation, main vein at base is closest to 146to 146B, lateral veins are close to 146A.

*Foliage texture.*—Smooth and flat.

*Petioles.*—Longest petioles are about 2.5 cm long, half-round, flat to slightly convex on upper surface, which is about 2 mm wide, depth of about 1.5 mm. Adaxial surface color appears to be closest to 146C; abaxial surface color appears to be close to 146C to 146D.

*Flower habit.*—Flowers are produced continuously throughout the flowering season.

*Natural flowering season.*—All year in greenhouse conditions, and the frost-free period from spring through fall, when planted outdoors.

*Duration of flower.*—Each flower generally lasts about 5 days at 75° F. maximum and 70° F. minimum temperature.

*Flowers borne.*—Above or beyond the foliage.

*Flower texture.*—Smooth and satiny.

*Flower color.*—Petals/petaloids — Adaxial surface is close to 75A. As the flower ages, the color at the edges fades toward 75B, and fades more towards the middle, changing to 69A to 69B. There is a basal spot that varies in intensity of color, generally being either close to 67A, or is more intense and close to 59B to 59C. The petaloids toward the center of the flower tend to have the basal spot color closest to 67A, while 59B to 59C tends to be more common on the outer petal's basal spot. Abaxial surface is closest to 75D, there is generally but not always a basal spot close to 67A.

*Quantity.*—Usually two or more open flowers per stem, and generally 15 or more from visible buds to fully mature flowers.

*Petal/petaloid count.*—Generally 25 or more.

*Size.*—Flowers are generally at least 3.5 cm in diameter; generally at least 1 cm deep with largest petals/petaloids. The largest petals/petaloids are generally at least 1.5 cm wide and at least 1.5 cm long; obovate to exaggerated obovate in shape with obtuse to retuse apex, entire margin, and cuneate to obtuse base. The above measurements refer to the average flowers.

*Flower buds.*—The buds before opening are about 1 cm in length; about 0.75 cm in diameter; shape is ovate. Bud color prior to opening is close to 145A on top and close to 145D on bottom.

*Peduncles.*—Generally at least 1.25 cm long; about 2 mm in diameter; colored close to 144B. Good strength.

*Pedicels.*—Generally two or more per peduncle. Each is generally at least 1.5 cm in length, and at least 1.5 mm in diameter. Color is close to 144B. Good strength.

*Calyx.*—Calyx consists of generally one sepal and one spur. The spur is generally at least 1.75 cm long, and about 2 mm in diameter at sepal end; shape is an acicular tapering tube about 1 mm in diameter at the apex, and it is attached toward the base of the sepal in a peltate manner. Color is close to 178A at apex, is an orangish-green that neither matches, nor is very close to any color in the chart, with the closest color in the chart being 166D at base. The apical color generally changes with maturity to close to 160A.

The sepal generally measures at least 0.75 cm wide and at least 1.1 cm long; ovate in shape with an acute apex, entire margin, and obtuse to cordate base; adaxial surface is lighter than 145D, with a base spot of close to 74A to 74B where the spur connects; the abaxial surface is close to 145D. The adaxial basal spot sometimes appears through to the abaxial side, giving an apparent spot that appears close to 70A where the spur attaches.

*Reproductive organs.*—The reproductive organs are replaced with sterile petaloids.

*Disease resistance.*—Disease resistance has not been tested.

*Dampness resistance.*—The plant has shown a good ability to hold the flowers in an outward manner during summer rains.

*Heat tolerance.*—The plant has shown a good tolerance to temperatures exceeding 100° F. at Rogue River by flowering continuously during temperatures as high as 113° F.

CHART 1

COMPARISON CHART TO PRIOR ART

| | 'TiLav Improved' | 'TiLav' |
|---|---|---|
| Stems-color | Color is translucent 146C to 146D with stippling on juvenile stems that is heaviest at the nodes which appear to be close to 178A. The stippling appears to be outgrown on mature stems as the stem color becomes solid 146C to 146D | 147A, spots of 187A |
| Foliage - Size | Size of largest is about 3 cm long; about 2.75 cm wide. | |
| Abaxial color | 148D | 148B, with marking close to 177A. |
| Foliage - Abaxial venation color | Main vein at base is closest to 146A to 146B, lateral veins are close to 146A. | 148A |
| Foliage - Adaxial color | Close to 146A | 147A |
| Foliage - Adaxial venation color | Close to 146D at base becoming barely distinguishable to undistinguishable towards the leaf margins; | 147A |
| Petiole - Size | Longest petioles about 2.5 cm long, about 2 mm wide, depth of about 1.5 mm. | |
| Adaxial color | Closest to 146C. | 146B, 178A |
| Petiole Abaxial color | Close to 146C ta 146D | 146B |
| Petal/Petaloid - Size | Generally at least 1.5 cm wide and at least 1.5 cm long. | 2 cm long, 2.5 cm wide. |
| Abaxial color | Closest to 75D, there is generally but not always a basal spot of close to 67A. | 75A |
| Petal/Petaloid Adaxial color | Close to 75A, as the flower ages, the color at the edges fades toward 75B and fades more towards the middle changing to 69A to 69B, there is a basal spot that varies in intensity of color generally being either close to 67A or is more intense and being close to 59B to 59C. The petaloids toward the center of the flower tend to have the basal spot color closest to 67A while 59B to 69C tends to be more common on the outer petals basal spot. | Mature flowers 74D with dark basal spot of 59B; Juvenile color 7AC with basal spot of 59B. |
| Peduncle - Size | Generally at least 1.25 cm long; about 2 min in diameter; | 2 cm long; 2.5 mm diameter. |
| Color | Close to 144B. | 145A |
| Pedicel - Size | Generally at least 1.5 cm in length, at least 1.5 mm in diameter. | 2 cm long; 1.5 mm diameter. |

CHART 1-continued

COMPARISON CHART TO PRIOR ART

| | 'TiLav Improved' | 'TiLav' |
|---|---|---|
| Color | Close to 144B. | 146B |
| Sepal - Size | Generally at least 0.75 cm wide, and at least 1.1 cm long; | 1 cm long; 0.8 cm wide. |
| Adaxial color | Lighter than 145D, with a base spot of close to 74A to 74B where the spur connects. | 145B to 145C with basal spot close to 183C. |
| Sepal Abaxial color | Close to 145D, sometimes an apparent spot that appears close to 70A where the spur attaches. | 145C |
| Spur - Size | Generally at least 1.75 cm long, and about 2 mm in diameter at sepal end, about 1 mm in diameter at the apex. | 3 cm long; 2 mm wide. |
| Color | Close to 178A at apex, is an orangish-green that neither matches, nor is very close to any color in the chart with the closest color in the chart being 166D at base. The spical color generally changes with maturity to close to 160A. | 146C at base, 183B at apex. |
| Buds - Size | About 1 cm. in length; about 0.75 cm. in diameter. | 0.8 cm long; 0.6 cm wide; 0.7 cm depth; |
| Color | Close to 145A on top and close to 145D on bottom. | 146B on top; 146D on bottom. |

COLOR CODE CHART

| | |
|---|---|
| Stems: | 146C, 146D, 178A |
| Foliage Abaxial surface: | 148D |
| Foliage Abaxial surface venation: | 146A, 146B |
| Foliage Adaxial surface: | 146A |
| Foliage Adaxial surface venation: | 146D |
| Petiole Abaxial surface: | 146C |
| Petiole Adaxial surface: | 146C, 146D |
| Petals/Petaloids Abaxial surface: | 75D, 67A |
| Petals/Petaloids Adaxial surface: | 75A, 75B, 69A, 69B, 67A, 59B, 59C, 67A, 59B, 59C |
| Buds: | 145A, 145D |
| Peduncles: | 144B |
| Pedicels: | 144B |
| Sepals adaxial surface: | 145D, 74A, 74B |
| Sepals abaxial surface: | 145D, 70A |
| Spur: | 178A, 166D, 160A |

It is claimed:

1. A new and distinct cultivar of double *impatiens walleriana* plant named 'TiLav Improved', as illustrated and described.

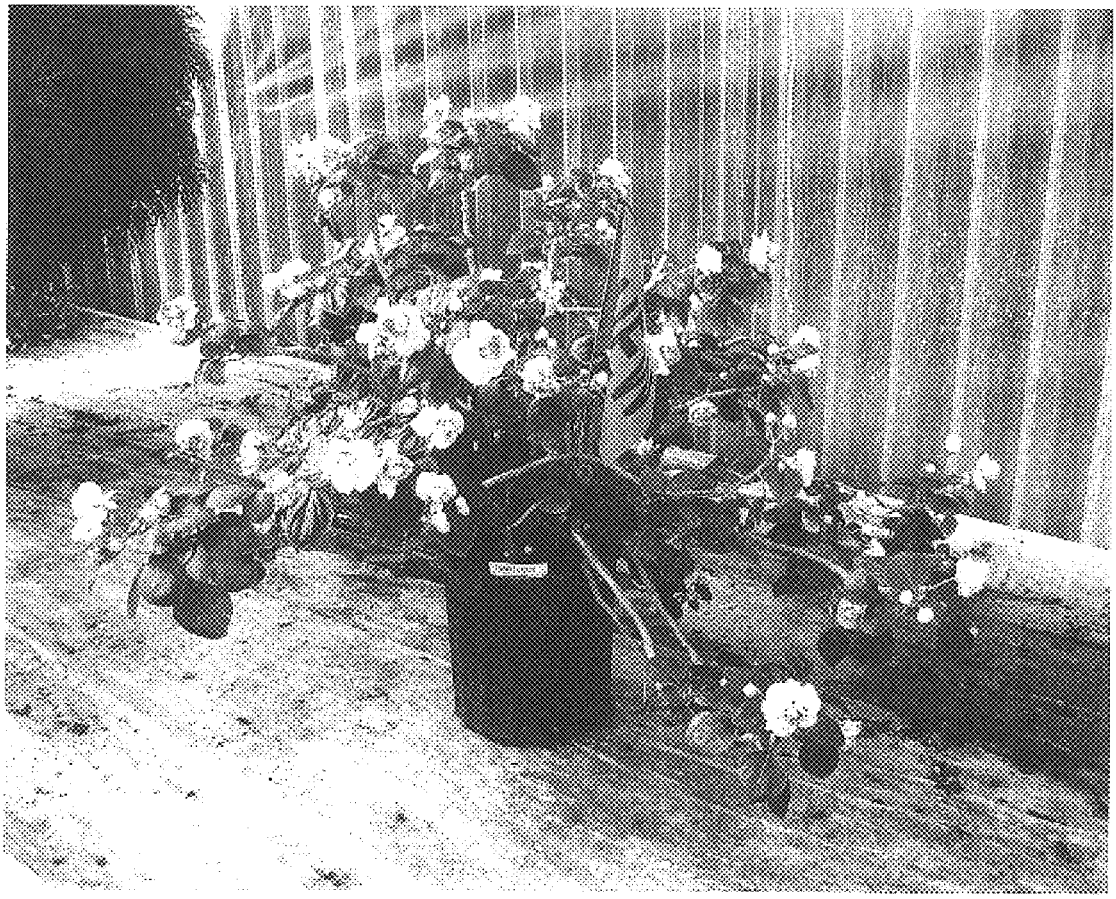

* * * * *